United States Patent [19]

Debono

[11] 4,293,485
[45] Oct. 6, 1981

[54] DERIVATIVES OF S31794/F-1 NUCLEUS

[75] Inventor: Manuel Debono, Indianapolis, Ind.

[73] Assignee: Eli Lilly and Company, Indianapolis, Ind.

[21] Appl. No.: 181,436

[22] Filed: Aug. 25, 1980

Related U.S. Application Data

[63] Continuation-in-part of Ser. No. 103,148, Dec. 13, 1979, abandoned.

[51] Int. Cl.$^3$ .................. C07C 103/52; A61K 37/00; C12P 21/04
[52] U.S. Cl. ............................ 260/112.5 R; 424/177; 435/71
[58] Field of Search ................. 260/112.5 R; 424/177; 435/71

[56] References Cited

U.S. PATENT DOCUMENTS

| | | | |
|---|---|---|---|
| 3,150,059 | 9/1964 | Kleinschmidt et al. | 260/112.5 R |
| 3,978,210 | 8/1976 | Mizuno et al. | 260/112.5 R |
| 4,024,245 | 5/1977 | Hoehn et al. | 260/112.5 R |
| 4,024,246 | 5/1977 | Higgens et al. | 260/112.5 R |
| 4,050,989 | 9/1977 | Kuwana et al. | 260/112.5 R |
| 4,173,629 | 11/1979 | Dreyfuss et al. | 260/112.5 R |

FOREIGN PATENT DOCUMENTS

| | | | |
|---|---|---|---|
| 834289 | 7/1975 | Belgium | 260/112.5 R |
| 859067 | 2/1977 | Belgium | 260/112.5 R |
| 866095 | 4/1977 | Belgium | 260/112.5 R |
| 851310 | 8/1977 | Belgium | 260/112.5 R |
| 38-405867 | 7/1963 | Japan | 260/112.5 R |
| 568386 | 4/1972 | Switzerland | 260/112.5 R |

OTHER PUBLICATIONS

T. Kato, et al., J. Antibiotics 29(12), 1339-1340, (1976).
S. Chihara, et al., Agr. Biol. Chem., 37(11), 2455-2463, (1973).
S. Chihara, et al., Ibid., 37(12), 2709-2717, (1973).
S. Chihara, et al., Ibid., 38(3), 521-529, (1974).
S. Chihara, et al., Ibid., 38(10), 1767-1777, (1974).
T. Suzuki, et al., J. Biochem., 56(4), 335-343, (1964).
J. M. Weber, et al., J. Antibiotics, 31(4), 373-374, (1978).
J. Shoji, et al., J. Antibiotics 28, 764-769, (1975).
J. Shoji, et al., Ibid., 29(4), 380-389, (1976).
J. Shoji, et al., Ibid., (12), 1268-1274, 1275-1280 (1976).
F. Benz, et al., Helv. Chim. Acta, 57, 2459, (1974).
C. Keller-Juslen, et al., Tetrahedron Letters, 4147-4150, 1976, vol. 46.
R. Traber, et al., Helv. Chim. Acta, 62, 1252, (1979).

*Primary Examiner*—Delbert R. Phillips
*Attorney, Agent, or Firm*—Nancy J. Harrison; Arthur R. Whale

[57] ABSTRACT

Compounds of the formula

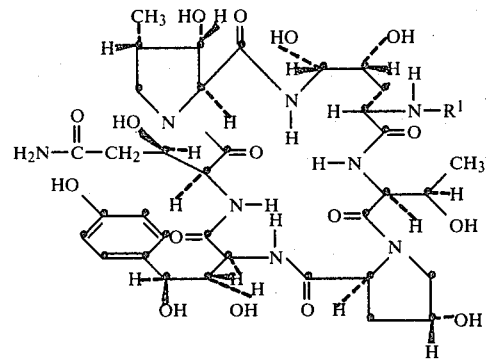

wherein $R^1$ is an N-alkanoyl amino acyl group of the formula

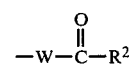

wherein:
W is a divalent aminoacyl radical of the formula:

(a)

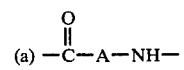

wherein A is $C_1$-$C_{10}$ alkylene or $C_5$-$C_6$ cycloalkylene;

(b)

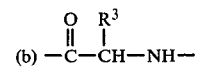

wherein $R^3$ is hydroxymethyl, hydroxyethyl, mercaptomethyl, mercaptoethyl, methylthioethyl, 2-thienyl, 3-indolemethyl, phenyl, benzyl, or substituted phenyl or substituted benzyl in which the benzene ring thereof is substituted with chloro, bromo, iodo, nitro, $C_1$-$C_3$ alkyl, hydroxy, $C_1$-$C_3$ alkylthio, carbamyl, or $C_1$-$C_3$ alkylcarbamyl;

(c)

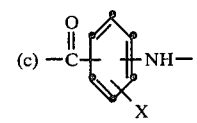

wherein X is hydrogen, chloro, bromo, iodo, nitro, $C_1$-$C_3$ alkyl, hydroxy, $C_1$-$C_3$ alkoxy, mercapto, $C_1$-$C_3$ alkylthio, carbamyl, or $C_1$-$C_3$ alkylcarbamyl;

(d)

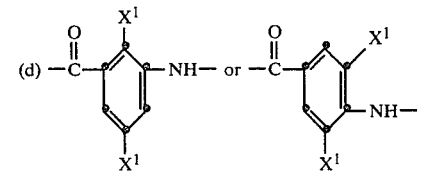

wherein $X^1$ is chloro, bromo, or iodo;
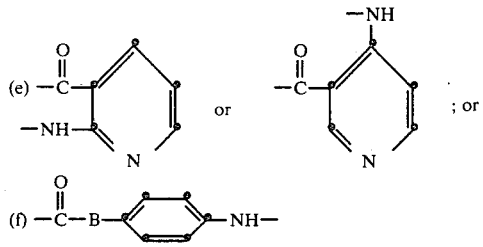
wherein B is a divalent radical of the formula:
$-(CH_2)_n-$, wherein n is an integer from 1 to 3; $-CH=CH-$; $-CH=CH-CH_2-$; or
$$-\overset{O}{\underset{\|}{C}}NHCH_2-$$
and $R^2$ is $C_1-C_{17}$ alkyl or $C_2-C_{17}$ alkenyl; have antifungal activity.
25 Claims, No Drawings

DERIVATIVES OF S31794/F-1 NUCLEUS

CROSS-REFERENCE TO RELATED APPLICATION

This application is a continuation-in-part of application Ser. No. 103,148, filed Dec. 13, 1979, now abandoned.

BACKGROUND OF THE INVENTION

This invention relates to novel semisynthetic antifungal compounds which are prepared by the acylation of the cyclic peptide nucleus produced by the enzymatic deacylation of antibiotic S31794/F-1.

Antibiotic S31794/F-1 is an antifungal cyclic peptide having the formula:

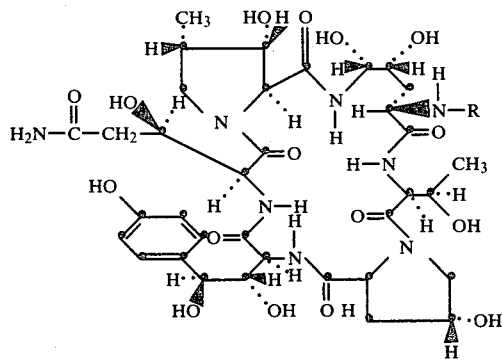

wherein R is the myristoyl group. Throughout this application, the cyclic peptide formulas, such as formula I, assume that the amino acids represented are in the L-configuration.

Antibiotic S31794/F-1, which is disclosed in German Offenlegungsschrift 2,628,965 and U.S. Pat. No. 4,173,629, is produced by *Acrophialophora limonispora nov. spec.* Dreyfuss et Muller NRRL 8095. S31794/F-1 has the following characteristics: m.p. 178°-180° C. (dec.) (amorphous) or 181°-183° C. (dec.) (crystalline); $[\alpha]_D^{20} -24°$ (c 0.5, CH$_3$OH) or $+37°$ (c 0.5, pyridine) (crystalline); UV absorption maxima in methanol at 194 nm ($E_{1cm}^{1\%}=807$), 225 nm (shoulder) $E_{1cm}^{1\%}=132$), 276 nm ($E_{1cm}^{1\%}=12.8$), 284 nm (shoulder) $E_{1cm}^{1\%}=10.5$); $^{13}$C-NMR spectrum in deuteromethanol (190 mg in 1.5 ml deuteromethanol, tetramethylsilane as internal standard) with the following characteristics (crystalline):

| PPM | PPM | PPM |
|---|---|---|
| 176.2 | 75.5 | 51.2 |
| 175.0 | 74.0 | 39.7 |
| 173.7 | 71.0 | 38.8 |
| 172.6 | 70.5 | 36.6 |
| 172.0 | 69.7 | 34.8 |
| 171.8 | 68.0 | 32.8 |
| 171.7 | 62.2 | 30.6 |
| 168.6 | 58.3 | 26.7 |
| 157.7 | 57.0 | 23.5 |
| 132.5 | 56.2 | 19.7 |
| 129.0 | 55.4 | 14.3 |
| 115.9 | 52.9 | 11.1 |
| 76.6 | | | an approximate elemental analysis (after drying crystalline material for two hours in a high vacuum at 100° C.) as follows: 55.5–56.5 percent carbon, 7.5–7.7 percent hydrogen, 10.5–10.8 percent nitrogen and 25.5–26.0 percent oxygen; is readily soluble in methanol, ethanol, pyridine, dimethyl sulfoxide and poorly soluble in water, chloroform, ethyl acetate, diethyl ether, benzene and hexane; and has antifungal activity, especially against *Candida albicans.*

Antibiotic S31794/F-1 is prepared by submerged aerobic cultivation of *Acrophialophora limonispora* NRRL 8095 as described in Examples 4 and 5. This microorganism is a part of the permanent culture collection of the Northern Regional Research Center, U.S. Department of Agriculture, Agricultural Research Culture Collection, North Central Region, Peoria, Ill. 61604, from which it is available to the public under the designated NRRL number.

Antibiotic S31794/F-1 has antifungal activity, particularly against Candida strains such as *Candida albicans.* Thus, production and isolation of the antibiotic can be monitored by bioautography using a Candida species such as *Candida albicans.*

In the antibiotic S31794/F-1 molecule (Formula I), the myristoyl side chain (R) is attached at the cyclic peptide nucleus at the α-amino group of the dihydroxyornithine residue. Surprisingly, it has been found that the myristoyl side chain can be cleaved from the nucleus by an enzyme without affecting the chemical intregity of the nucleus. The enzyme employed to effect the deacylation reaction is produced by a microorganism of the family Actinoplanaceae, preferably the microorganism *Actinoplanes utahensis* NRRL 12052, or a variant thereof. To accomplish deacylation, antibiotic S31794/F-1 is added to a culture of the microorganism and the culture is allowed to incubate with the substrate until the deacylation is substantially complete. The cyclic nucleus thereby obtained is separated from the fermentation broth by methods known in the art. Unlike antibiotic S31794/F-1, the cyclic nucleus (lacking the linoleoyl side chain) is substantially devoid of antifungal activity.

The cyclic nucleus afforded by the aforedescribed enzymatic deacylation of antibiotic S31794/F-1 is depicted in Formula II.

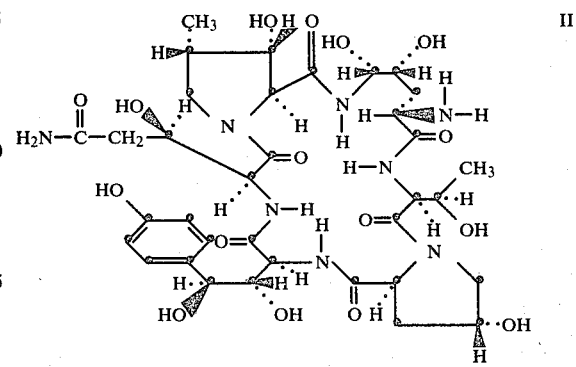

S31794/F-1 nucleus has an empirical formula of C$_{35}$H$_{52}$N$_8$O$_{16}$ and a molecular weight of 840.87.

Removal of the side chain group affords a free primary α-amino group in the dihydroxyornithine residue of the cyclic peptide. For convenience, the compound having the structure given in Formula II will be referred to herein as "S31794/F-1 nucleus." As will be apparent to those skilled in the art, S31794/F-1 nucleus can be obtained either in the form of the free amine or of the acid addition salt. Although any suitable acid addition salt may be employed, those which are non-toxic and pharmaceutically acceptable are preferred.

The method of preparing S31794/F-1 nucleus from antibiotic S31794/F-1 by means of fermentation using *Actinoplanes utahensis* NRRL 12052 is described in the co-pending application of Bernard J. Abbott and David S. Fukuda, entitled "S 31794/F-1 NUCLEUS", Ser. No. 103,313 which was filed Dec. 13, 1979. A continuation-in-part application of this application, with corresponding Ser. No. 181,036, is being filed herewith this even date, the full disclosure of which is incorporated herein by reference. Example 3 herein, illustrates the preparation of S31794/F-1 nucleus by fermentation using antibiotic S31974/F-1 as the substrate and *Actinoplanes utahensis* NRRL 12052 as the microorganism.

The enzyme produced by *Actinoplanes utahensis* NRRL 12052 may be the same enzyme which has been used to deacylate penicillins (see Walter J. Kleinschmidt, Walter E. Wright, Frederick W. Kavanagh, and William M. Stark, U.S. Pat. No. 3,150,059, issued Sept. 22, 1964).

Cultures of representative species of Actinoplanaceae are available to the public from the Northern Regional Research Laboratory under the following accession numbers:

| | |
|---|---|
| *Actinoplanes utahensis* | NRRL 12052 |
| *Actinoplanes missouriensis* | NRRL 12053 |
| Actinoplanes sp. | NRRL 8122 |
| Actinoplanes sp. | NRRL 12065 |
| *Streptosporangium roseum* var. *hollandesis* | NRRL 12064 |

The effectiveness of any given strain of microorganism within the family Actinoplanaceae for carrying out the deacylation of this invention is determined by the following procedure. A suitable growth medium is inoculated with the microorganism. The culture is incubated at about 28° C. for two or three days on a rotary shaker. One of the substrate antibiotics is then added to the culture. The pH of the fermentation medium is maintained at about pH 6.5. The culture is monitored for activity using a *Candida albicans* assay. Loss of antibiotic activity is an indication that the microorganism produces the requisite enzyme for deacylation. This must be verified, however, using one of the following methods: (1) analysis by HPLC for presence of the intact nucleus; or (2) re-acylation with an appropriate side chain (e.g. linoleoyl, stearoyl, or palmitoyl) to restore activity.

SUMMARY OF THE INVENTION

The invention sought to be patented comprehends novel compounds derived by acylating S31794/F-1 nucleus (Formula II). The compounds of the present invention have the chemical structure depicted in Formula III:

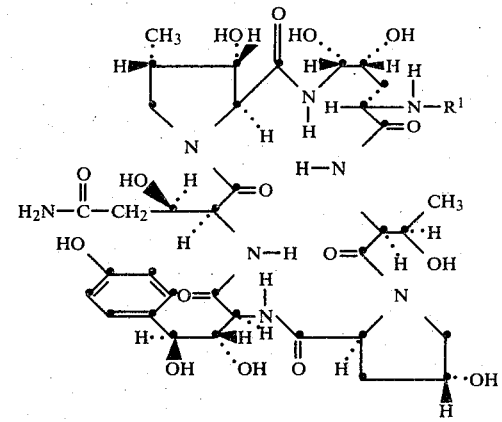

wherein $R^1$ is an N-alkanoyl amino acyl group of the formula

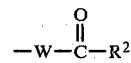

wherein:

W is a divalent aminoacyl radical of the formula:

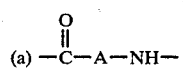

wherein A is $C_1$–$C_{10}$ alkylene or $C_5$–$C_6$ cycloalkylene;

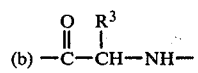

wherein $R^3$ is hydroxymethyl, hydroxyethyl, mercaptomethyl, mercaptoethyl, methylthioethyl, 2-thienyl, 3-indolemethyl, benzyl, or substituted phenyl or substituted benzyl in which the benzene ring thereof is substituted with chloro, bromo, iodo, nitro, $C_1$–$C_3$ alkyl, hydroxy, $C_1$–$C_3$ alkylthio, carbamyl, or $C_1$–$C_3$ alkylcarbamyl;

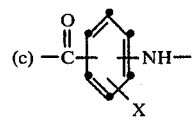

wherein X is hydrogen, chloro, bromo, iodo, nitro, $C_1$–$C_3$ alkyl, hydroxy, $C_1$–$C_3$ alkoxy, mercapto, $C_1$–$C_3$ alkylthio, carbamyl, or $C_1$–$C_3$ alkylcarbamyl;

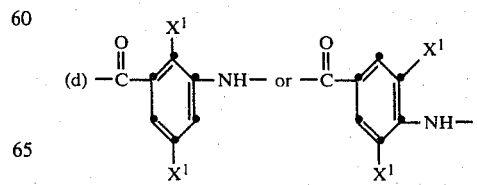

wherein $X^1$ is chloro, bromo, or iodo;

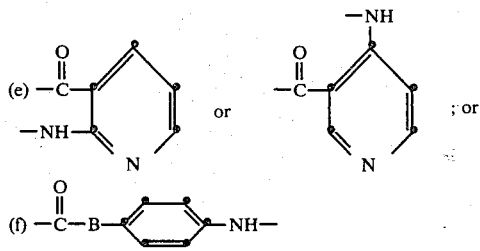

wherein B is a divalent radical of the formula: $-(CH_2)_n-$, wherein n is an integer from 1 to 3; $-CH=CH-$; $-CH=CH-CH_2-$; or

and $R^2$ is $C_1$-$C_{17}$ alkyl or $C_2$-$C_{17}$ alkenyl.

As employed herein the terms "alkylene", "alkyl", "alkoxy", "alkylthio", and "alkenyl" comprehend both straight and branched hydrocarbon chains. "Alkyl" means a univalent saturated hydrocarbon radical. "Alkenyl" means a univalent unsaturated hydrocarbon radical containing one, two, or three double bonds, which may be oriented in the cis or trans configuration. "Alkylene" means a divalent saturated hydrocarbon radical. "Cycloalkylene" means a divalent cyclic saturated hydrocarbon radical.

Illustrative $C_1$-$C_{10}$ alkylene radicals, which are preferred for purposes of this invention are: $-CH_2-$;

in which $R^5$ is $C_1$-$C_4$ alkyl (i.e., methyl, ethyl, n-propyl, i-propyl, n-butyl, t-butyl, i-butyl, or 1-methylpropyl); $-(CH_2)_m-$ in which m is an integer from 2 to 10; and $CH_3-(CH_2)_q-CH-(CH_2)_p-$, in which p is an integer from 1 to 8 and q is an integer from 0 to 7, provided that n+m must be no greater than 8.

Illustrative $C_1$-$C_{17}$ alkyl groups which are preferred for the purposes of this invention are:

(a) $CH_3-$;

(b) $-(CH_2)_nCH_3$ wherein n is an integer from 1 to 16; and (c)

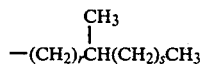

wherein r and s are independently, an integer from 0 to 14 provided that r+s can be no greater than 14.

Illustrative $C_2$-$C_{17}$ alkenyl radicals, which are preferred for the purpose of this invention, are:

(a) $-(CH_2)_t-CH=CH-(CH_2)_u-CH_3$ wherein t and u are independently, an integer from 0 to 14 provided that t+u can be no greater than 14.

(b) $-(CH_2)_v-CH=CH-(CH_2)_y-CH=CH-(CH_2)_z-CH_3$ wherein v and z are independently, an integer from 0 to 11 and y is an integer from 1 to 12 provided that v+y+z can be no greater than 11.

In particular, the following embodiments of the $C_1$-$C_{17}$ alkyl groups are preferred:

$CH_3-$
$CH_3(CH_2)_5-$
$CH_3(CH_2)_6-$
$CH_3(CH_2)_8-$
$CH_3(CH_2)_{10}-$
$CH_3(CH_2)_{12}-$
$CH_3(CH_2)_{14}-$
$CH_3(CH_2)_{16}-$

In particular, the following embodiments of the $C_2$-$C_{17}$ alkenyl groups are preferred:

cis-$CH_3(CH_2)_5CH=CH(CH_2)_7-$
trans-$CH_3(CH_2)_5CH=CH(CH_2)_7-$
cis-$CH_3(CH_2)_{10}CH=CH(CH_2)_4-$
trans-$CH_3(CH_2)_{10}CH=CH(CH_2)_4-$
cis-$CH_3(CH_2)_7CH=CH(CH_2)_7-$
trans-$CH_3(CH_2)_7CH=CH(CH_2)_7-$
cis-$CH_3(CH_2)_5CH=CH(CH_2)_9-$
trans-$CH_3(CH_2)_5CH=CH(CH_2)_9-$
cis, cis-$CH_3(CH_2)_4CH=CHCH_2CH=CH(CH_2)_7-$
trans, trans-$CH_3(CH_2)_4CH=CHCH_2CH=CH(CH_2)_7-$
cis,cis,cis-$CH_3CH_2CH=CHCH_2CH=CHCH_2CH=CH-(CH_2)_7-$.

When "W" is a divalent radical of the formula

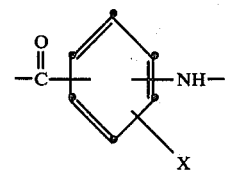

it will be recognized by those skilled in the art that the

function and the $-NH-$ function may be oriented on the benzene ring in the ortho, meta, or para configuration relative to each other. The substituent represented by X may be substituted at any available position of the benzene ring. Preferred embodiments are those in which X is hydrogen and the

and $-NH-$ functions are oriented in the para configuration.

The terms "substituted phenyl" and "substituted benzyl", as defined by $R_3$ in Formula III, contemplate substitution of a group at any of the available positions in the benzene ring—i.e. the substituent may be in the ortho, meta, or para configuration. The term "$C_1$-$C_3$ alkyl" as defined by $R_3$ or X in Formula III includes the methyl, ethyl, n-propyl, or i-propyl groups.

DETAILED DESCRIPTION OF THE INVENTION

The compounds of Formula III inhibit the growth of pathogenic fungi, and are useful, therefore, for controlling the growth of fungi on environmental surfaces (as an antiseptic) or in treating infections caused by fungi. In particular, the compounds are active against *Candida albicans* and are, thus especially useful for treating candidosis. The activity of the compounds can be assessed in standard microbiological test procedures, such as in vitro in agar plate disc diffusion tests or in agar tube dilution tests, or in vivo in tests in mice infected in *C. albicans*. The compounds are also active against *Trichophyton mentagrophytes* (a dermatophytic organism), *Saccharomyces pastorianus*, and *Neurospora crassa*.

The compounds of Formula III are prepared by acylating S31794/F-1 nucleus at the α-amino group of dihydroxyornithine with the appropriate N-alkanoyl aminoacyl or N-alkenoyl amino acyl side chain using methods conventional in the art for forming an amide bond. The acylation is accomplished, in general, by reacting the nucleus with an activated derivative of the acid (Formula IV) corresponding to the desired acyl side chain group.

    IV (W and $R^2$ have the meaning described herein supra).

By the term "activated derivative" is meant a derivative which renders the carboxyl function of the acylating agent reactive to coupling with the primary amino group to form the amide bond which links the acyl side chain to the nucleus. Suitable activated derivatives, their methods of preparation, and their methods of use as acylating agents for a primary amine will be recognized by those skilled in the art. Preferred activated derivatives are: (a) an acid halide (e.g. acid choride), (b) an acid anhydride (e.g. an alkoxyformic acid anhydride or aryloxyformic acid anhydride) or (c) an activated ester (e.g. a 2,4,5-trichlorophenyl ester, a N-hydroxybenztriazole ester, or an N-hydroxysuccinimide ester). Other methods for activating the carboxyl function include reaction of the carboxylic acid with a carbonyldiimide (e.g. N,N-dicyclohexylcarbodiimide or N,N'-diisopropylcarbodiimide) to give a reactive intermediate which, because of instability, is not isolated, the reaction with the primary amine being carried out in situ.

A preferred method for preparing the compounds of Formula III is by the active ester method. The use of the 2,4,5-trichlorophenyl ester of the desired N-alkanoylamino acid or N-alkenoylamio acid (Formula IV) as the acylating agent is most preferred. In this method, an excess amount of the active ester is reacted with the nucleus at room temperature in a nonreactive organic solvent such as dimethyl formamide (DMF). The reaction time is not critical, although a time of about 15 to about 18 hours is preferred. At the conclusion of the reaction, the solvent is removed, and the residue is purified such as by column chromatography using silica gel as the stationary phase and a mixture of ethyl acetate/methanol (3:2, v/v) as the solvent system.

The 2,4,5-trichlorophenyl esters of the N-alkanoylamino acids or N-alkanoylamino acids can be prepared conveniently by treating the desired amino acid (Formula IV) with 2,4,5-trichlorophenol in the presence of a coupling agent, such as N,N'-dicyclohexylcarbodiimide. Other methods suitable for preparing amino acid esters will be apparent to those skilled in the art.

The N-alkanoylamino acids or N-alkenoylamino acids are either known compounds or they can be made by acylating the appropriate amino acid with the appropriate alkanoyl or alkenoyl group using conventional methods, such as those described herein supra. A preferred way of preparing the N-alkanoylamino acids is by treating the appropriate amino acid with an alkanoic acid chloride in pyridine. The alkanoic acids, the activated derivatives thereof, and the amino acids employed in the preparation of the products of this invention are either known compounds or they can be made by known methods or by modification of known methods which will be apparent to those skilled in the art.

If a particular amino acid contains an acylable functional group other than the amino group, it will be understood by those skilled in the art that such a group must be protected prior to reaction of the amino acid with the reagent employed to attach the alkanoyl or alkenoyl group. Suitable protecting groups can be any group known in the art to be useful for the protection of a side chain functional group in peptide synthesis. Such groups are well known, and the selection of a particular protecting group and its method of use will be readily known to one skilled in the art [see, for example, "Protective Groups In Organic Chemistry", M. McOmie, Editor, Plenum Press, N.Y., 1973].

It will be recognized that certain amino acids employed in the synthesis of the products of this invention may exist in optically active forms, and both the natural configuration (L-configuration) and unnatural configuration (D-configuration) may be employed as starting materials and will give products which are within the contemplation of this invention.

When employed systemically, the dosage of the compounds of Formula III will vary according to the particular compound being employed, the severity and nature of the infection, and the physical condition of the subject being treated. Therapy should be initiated at low dosages, the dosage being increased until the desired antifungal effect is obtained. The compounds can be administered intravenously or intramuscularly by injection in the form of a sterile aqueous solution or suspension to which may be added, if desired, various conventional pharmaceutically acceptable preserving, buffering, solubilizing, or suspending agents. Other additives, such as saline or glucose may be added to make the solutions isotonic. The proportions and nature of such additives will be apparent to those skilled in the art.

When employed to treated vaginal candida infections, the compounds of Formula III can be administered in combination with pharmaceutically acceptable conventional excipients suitable for intravaginal use. Formulations adapted for intravaginal administration will be known to those skilled in the art.

One of the methods of making and using the compounds of the present invention is illustrated in the following examples:

EXAMPLE 1

The following procedure, which give the preparation of the compound of Formula III wherein $R^1$ is N-(n- dodecanoyl)-p-aminobenzoyl, illustrates a method of preparation of the compounds of Formula III.

A. Preparation of N-(n-dodecanoyl)-p-aminobenzoic acid n-Dodecanoyl chloride (8.74 g.; 40 mmoles) is added dropwise to a solution of p-aminobenzoic acid (40 mmoles) dissolved in pyridine (100 ml.). The mixture is stirred for 3 hours and poured into water (3 l.). The precipitate which forms is filtered and dried in vacuo to give N-(n-dodecanoyl)-p-aminobenzoic acid (11.01 g.).

B. Preparation of the 2,4,5-trichlorophenyl ester of N-dodecanoyl-p-aminobenzoic acid N-(n-Dodecanoyl)-p-aminobenzoic acid (11.01 g.; 34.5 mmoles), 2,4,5-trichlorophenol (7.5 g.; 38 mmoles), and dicyclohexylcarbodiimide (6.94 g.; 34.5 mmoles) are dissolved in methylene chloride (250 ml). The mixture is stirred at room temperature for 3.5 hours and then filtered. The filtrate is evaporated in vacuo to give a residue which is crystallized from acetonitrile/water to afford the 2,4,5-trichlorophenyl ester of N-(n-dodecanoyl)-p-aminobenzoic acid (12.84 g.).

C. Acylation of S31794/F-1 nucleus

S317941F-1 nucleus (10.2 mmoles) and the 2,4,5-trichlorophenyl ester of N-(n-dodecanoyl)-p-aminobenzoic acid (10.2 mmoles) are dissolved in dimethylformamide (100 ml.). The solution is stirred at room temperature for 15 hours. Solvent is removed in vacuo to give a residue which is washed twice with diethylether. The washes are discarded. The washed residue is dissolved in methanol (50 ml.) and is purified by reversed phase HPLC by means of a "Prep LC/System 500" unit (Waters Associates, Inc., Milford, Mass.) using a Prep Pak-500/C18 column (Water Associates, Inc.) as the stationary phase. The column is eluted isocratically with $H_2O/CH_3OH/CH_3CN$ (25:65:10 v/v) at 500 psi. The fractions are analyzed by TLC using silica gel plates and $H_2O/CH_3OH/CH_3CN$ (25:65:10 v/v) as the solvent system. Fractions containing the desired products are combined and lyophilized to give the N-(n-dodecanoyl)-p-aminobenzoyl derivative of S31794/F-1 nucleus.

EXAMPLE 2

The method described in Example 1, with minor changes, can be used to synthesize additional derivatives of the S31794/F-1 nucleus. The substitution of the appropriate acyl chloride and amino acid in Step A, the substitution of the appropriate N-alkanoyl amino acid, (plus the use of tetrahydrofuran as the solvent for N-alkanoyl monochloro-substituted aminobenzoic acids), in Step B, and the substitution of the appropriate 2,4,5 trichlorophenyl ester in Step C of Example 1 can yield the derivatives of the S31794/F-1 nucleus shown below:

N-Alkanoylamino Acid Derivatives of S31794/F-1 Nucleus

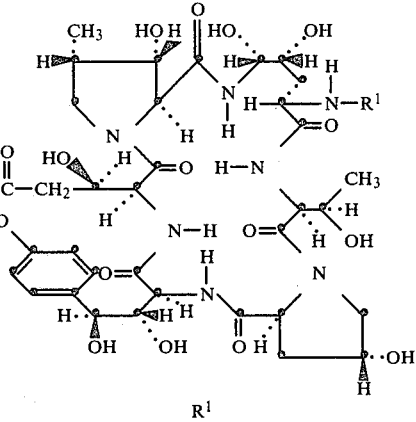

III $R^1$ $CH_3(CH_2)_{10}CONHCH(CH_2C_6H_5)CO-$
$CH_3(CH_2)_{10}CONH(CH_2)_4-CO-$
$(CH_3(CH_2)_{10}CONH(CH_2)_{10}-CO-$

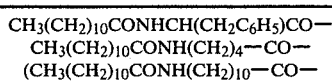

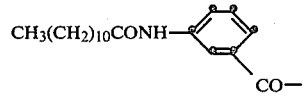

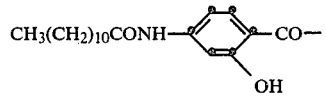

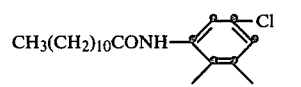

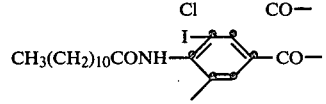

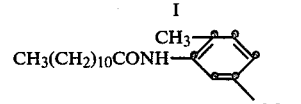

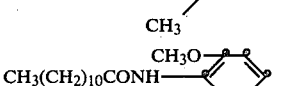

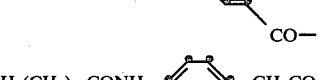

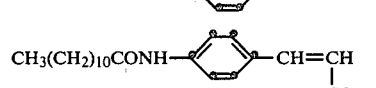

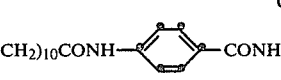

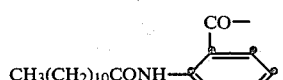

$CH_3(CH_2)_5CONH(CH_2)_{10}-CO-$

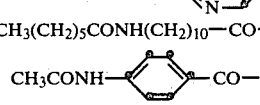

N-Alkanoylamino Acid Derivatives of S31794/F-1 Nucleus

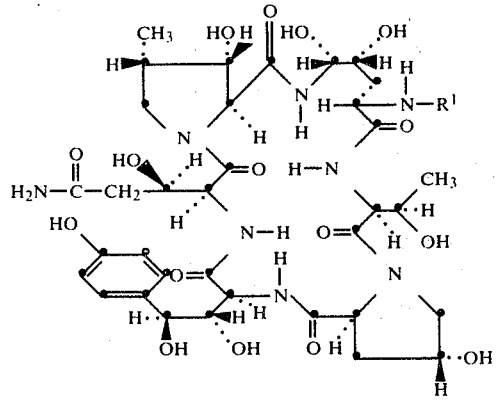   III

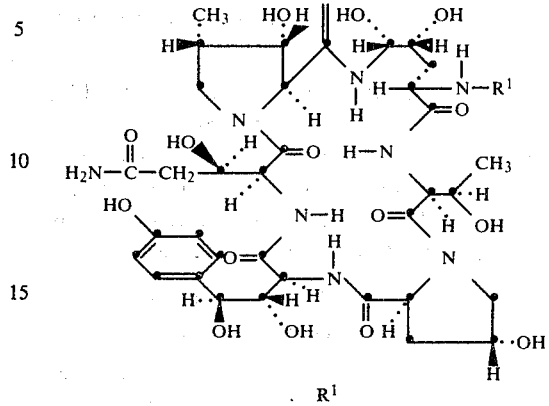   III

| R[1] | |
|---|---|
|  | |
| 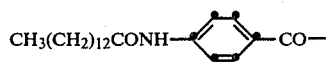 | |
| 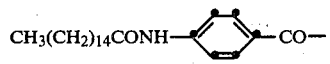 | |
| 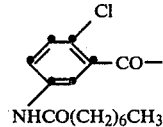 | |
| 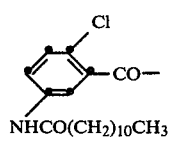 | |
| 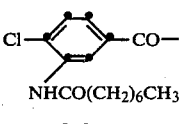 | |
| 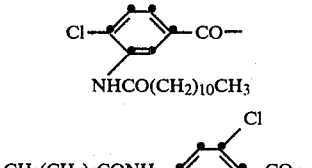 | |
| 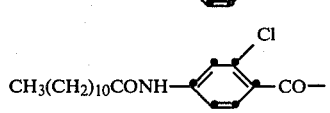 | |
| 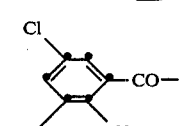 | |
| 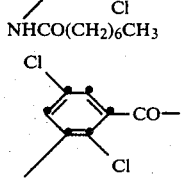 | |
| 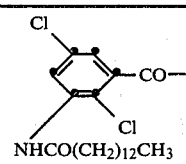 | |

EXAMPLE 3

Preparation of S31794/F-1 Nucleus

A. Fermentation of *Actinoplanes utahensis* NRRL 12052

A stock culture of *Actinoplanes utahensis* NRRL 12052 is prepared and maintained on an agar slant. The medium used to prepare the slant is selected from one of the following:

| MEDIUM A | |
|---|---|
| Ingredient | Amount |
| Baby oatmeal | 60.0 g |
| Yeast | 2.5 g |
| K$_2$HPO$_4$ | 1.0 g |
| Czapek's mineral stock* | 5.0 ml |
| Agar | 25.0 g |
| Deionized water | q.s. to 1 liter | pH before autoclaving is about 5.9; adjust to pH 7.2 by addition of NaOH; after autoclaving, pH is about 6.7.
*Czapek's mineral stock has the following composition:

| Ingredient | Amount |
|---|---|
| FeSO$_4$ . 7H$_2$O (dissolved in 2 ml conc HCl) | 2 g |
| KCl | 100 g |
| MgSO$_4$ . 7H$_2$O | 100 g |
| Deionized water | q.s. to 1 liter |

| MEDIUM B | |
|---|---|
| Ingredient | Amount |
| Potato dextrin | 5.0 g |
| Yeast extract | 0.5 g |
| Enzymatic hydrolysate of casein* | 3.0 g |
| Beef extract | 0.5 g |
| Dextrose | 12.5 g |
| Corn starch | 5.0 g |
| Meat peptone | 5.0 g |
| Blackstrap molasses | 2.5 g |
| MgSO$_4$ . 7H$_2$O | 0.25 g |
| CaCO$_3$ | 1.0 g |
| Czapek's mineral stock | 2.0 ml |
| Agar | 20.0 g |
| Deionized water | q.s. to 1 liter |

| MEDIUM B | |
|---|---|
| Ingredient | Amount |
| *N-Z-Amine A, Humko Sheffield Chemical, Lyndhurst, N.J. | |

The slant is inoculated with *Actinoplanes utahensis* NRRL 12052, and the inoculated slant is incubated at 30° C. for about 8 to 10 days. About ½ of the slant growth is used to inoculate 50 ml of a vegetative medium having the following composition:

| Ingredient | Amount |
|---|---|
| Baby oatmeal | 20.0 g |
| Sucrose | 20.0 g |
| Yeast | 2.5 g |
| Distiller's Dried Grain* | 5.0 g |
| K$_2$HPO$_4$ | 1.0 g |
| Czapek's mineral stock | 5.0 ml |
| Deionized water | q.s. to 1 liter | adjust to pH 7.4 with NaOH; after autoclaving, pH is about 6.8.
*National Distillers Products Co., 99 Park Ave., New York, N.Y.

The inoculated vegetative medium is incubated in a 250-ml wide-mouth Erlenmeyer flask at 30° C. for about 72 hours on a shaker rotating through an arc two inches in diameter at 250 RPM.

This incubated vegetative medium may be used directly to inoculate a second-stage vegetative medium. Alternatively and preferably, it can be stored for later use by maintaining the culture in the vapor phase of liquid nitrogen. The culture is prepared for such storage in multiple small vials as follows: In each vial is placed 2 ml of incubated vegetative medium and 2 ml of a glycerol-lactose solution [see W. A. Dailey and C. E. Higgens, "Preservation and Storage of Microorganisms in the Gas Phase of Liquid Nitrogen, *Cryobiol* 10, 364–367 (1973) for details]. The prepared suspensions are stored in the vapor phase of liquid nitrogen.

A stored suspension (1 ml) thus prepared is used to inoculate 50 ml of a first-stage vegetative medium (having the composition earlier described). The inoculated first-stage vegetative medium is incubated as above-described.

In order to provide a larger volume of inoculum, 10 ml of the incubated first-stage vegetative medium is used to inoculate 400 ml of a second-stage vegetative medium having the same composition as the first-stage vegetative medium. The second-stage medium is incubated in a two-liter wide-mouth Erlenmeyer flask at 30° C. for about 48 hours on a shaker rotating through an arc two inches in diameter at 250 RPM.

Incubated second-stage vegetative medium (800 ml), prepared as above-described, is used to inoculate 100 liters of sterile production medium selected from one of the following:

| MEDIUM I | |
|---|---|
| Ingredient | Amount (g/L) |
| Peanut meal | 10.0 |
| Soluble meat peptone | 5.0 |
| Sucrose | 20.0 |
| KH$_2$PO$_4$ | 0.5 |
| K$_2$HPO$_4$ | 1.2 |
| MgSO$_4$ . 7H$_2$O | 0.25 |
| Tap water | q.s. to 1 liter |

The pH of the medium is about 6.9 after sterilization by autoclaving at 121° C. for 45 minutes at about 16–18 psi.

| MEDIUM II | |
|---|---|
| Ingredient | Amount (g/L) |
| Sucrose | 30.0 |
| Peptone | 5.0 |
| K$_2$HPO$_4$ | 1.0 |
| KCl | 0.5 |
| MgSO$_4$ . 7H$_2$O | 0.5 |
| FeSO$_4$ . 7H$_2$O | 0.002 |
| Deionized water | q.s. to 1 liter |

Adjust to pH 7.0 with HCl; after autoclaving, pH is about 7.0.

| MEDIUM III | |
|---|---|
| Ingredient | Amount (g/L) |
| Glucose | 20.0 |
| NH$_4$Cl | 3.0 |
| Na$_2$SO$_4$ | 2.0 |
| ZnCl$_2$ | 0.019 |
| MgCl$_2$ . 6H$_2$O | 0.304 |
| FeCl$_3$ . 6H$_2$O | 0.062 |
| MnCl$_2$ . 4H$_2$O | 0.035 |
| CuCl$_2$ . 2H$_2$O | 0.005 |
| CaCO$_3$ | 6.0 |
| KH$_2$PO$_4$* | 0.67 |
| Tap water | q.s. to 1 liter |

*Sterilized separately and added aseptically Final pH about 6.6.

The inoculated production medium is allowed to ferment in a 165-liter fermentation tank at a temperature of about 30° C. for about 42 hours. The fermentation medium is stirred with conventional agitators at about 200 RPM and aerated with sterile air to maintain the dissolved oxygen level above 30% of air saturation at atmospheric pressure.

B. Deacylation of Antibiotic S31794/F-I

A fermentation of *A. utahensis* is carried out as described in Sect. A, using production medium I. After the culture is incubated for about 48 hours, antibiotic S31794F-1, dissolved in a small amount of methanol, is added to the fermentation medium.

Deacylation of S31794/F-1 is monitored by paper-disc assay against *Candida albicans*. The fermentation is allowed to continue until deacylation is complete as indicated by disappearance of activity.

C. Isolation of S31794/F-1 Nucleus

Whole fermentation broth, obtained as described in Sect. B is filtered. The mycelial cake is discarded. The clear filtrate thus obtained is passed through a column containing HP-20 resin (DIAION High Porous Polymer, HP-Series, Mitsubishi Chemical Industries Limited, Tokyo, Japan). The effluent thus obtained is discarded. The column is then washed with up to eight column volumes of deionized water at pH 6.5–7.5 to remove residual filtered broth. This wash water is discarded. The column is then eluted with a water:methanol (7:3) solution. Elution is monitored using the following procedure: Two aliquots are taken from each eluted fraction. One of the aliquots is concentrated to a small volume and is treated with an acid chloride such as myristoyl chloride. This product and the other (untreated) aliquot are assayed for activity against *Candida albicans*. If the untreated aliquot does not have activity and the acylated aliquot does have activity, the fraction contains S31794/F-1 nucleus. The eluate containing S31794/F-1 nucleus is concentrated under vacuum to a small volume and lyophilized to give crude nucleus.

D. Purification of S31794F-1 Nucleus by Reversed-Phase Liquid Chromatography

Crude S31794/F-1 nucleus, obtained as described in Section C, is dissolved in water:acetonitrile:acetic acid:pyridine (96:2:1:1). This solution is chromatographed on a column filled with Lichroprep RP-18, particle size 25–40 microns (MC/B Manufacturing Chemists, Inc. E/M, Cincinnati, OH). The column is part of a Chromatospac Prep 100 unit (Jobin Yvon, 16–18 Rue du Canal 91160 Longjumeau, France). The column is operated at a pressure of 90–100 psi, giving a flow rate of about 60 ml/minute, using the same solvent. Separation is monitored at 280 nm using a UV monitor (ISCO Absorption Monitor Model UA-5, Instrumentation Specialties Co., 4700 Superior Ave., Lincoln, Nebraska 68504) with an optical unit (ISCO Type 6).

On the basis of absorption at 280 nm, fractions containing S31794/F-1 nucleus are combined, evaporated under vacuum and lyophilized to give purified S31794/F-1 nucleus.

EXAMPLE 4

Preparation of Antibiotic S31794/F-1

Antibiotic S31794/F-1 is produced by submerged culture of *Acrophialophora limonispora* NRRL 8095 with stirring, shaking, and/or aeration at pH 3–8, preferably pH 5–7, and at 15°–30° C., preferably at 18°–27° C., for from 48 to 360 hours, preferably from 120 to 288 hours.

Antibiotic S31794/F-1 is isolated by treating the culture broth (90 L) with ethyl acetate:isopropanol (4:1, 90 L) and homogenizing for 30 minutes at room temperature. The organic phase is separated and evaporated under vacuum at about 40° C. The residue thus obtained is chromatographed on a 10-fold amount of silica gel, using $CHCl_3:CH_3OH$ (95:5 to 60:40). Fractions which have antifungal activity are combined and chromatographed on a 100-fold amount of "Sephadex LH-20" with methanol. Fractions from the Sephadex column which have antifungal activity are combined and rechromatographed on a 100-fold amount of silica gel (0.05–0.2 mm) with a $CHCl_3:CH_3OH:H_2O$ (71:25:4) solvent system. The fractions eluted which have antifungal activity are combined and evaporated under vacuum to give crude antibiotic S31794/F-1. This product is dissolved in small amounts of methanol and precipitated with diethyl ether to give S31794/F-1 as a white amorphous powder, mp 178°–180° C. (dec.) after drying in high vacuum at 25°–30° C. Crystallization from a 10-fold amount of ethyl acetate:methanol:water (80:12:8) gives crystalline S31794/F-1, mp 181°–183° C. (dec) after drying in high vaccuum at 20° C.

EXAMPLE 5

Isolation of Antibiotic S31794/F-1

Crude antibiotic S31794/F-1, obtained as described in Example 4 after chromatography over Sephadex, is introduced onto a silica-gel column (Michel-Miller Column) through a loop with the aid of a valve system. The column is packed with LP-1/$C_{18}$ silica-gel reversed-phase resin (10–20 microns), prepared as described in Example 6, in chloroform:methanol:water (71:25:4) through a loop with the aid of a valve system. The slurry packing procedure described in Example 7 is used. The solvent is moved through the column using an F.M.I. pump with valveless piston design. Elution of the antibiotic is monitored using a UV monitor at 280 nm as in Example 3. Fractions having antifungal activity are combined and concentrated under vacuum to give antibiotic S31794/F-1.

S31794/F-1 has $R_f$ values as follow on silica-gel thin-layer chromatography (Merck, 0.25 mm):

| Solvent System | $R_f$ Value |
|---|---|
| Chloroform:methanol:water (71:25:4) | 0.17 |
| Chloroform:methanol:conc. acetic acid (70:29:1) | 0.19 |
| Chloroform:methanol (2:1) | 0.27 |

S31794/F-1 can also be detected by iodine vapor.

EXAMPLE 6

Preparation of Silica Gel/$C_{18}$ Reversed Phase Resin

Step 1: Hydrolysis

LP-1 silica gel (1000 g from Quantum Corp., now Whatman) is added to a mixture of concentrated sulfuric acid (1650 ml) and concentrated nitric acid (1650 ml) is a 5-L round-bottom flask and shaken for proper suspension. The mixture is heated on a steam bath overnight (16 hours) with a water-jacketed condenser attached to the flask.

The mixture is cooled in an ice bath and carefully filtered using a sintered-glass funnel. The silica gel is washed with deionized water until the pH is neutral. The silica gel is then washed with acetone (4 L) and dried under vacuum at 100° C. for 2 days.

Step 2: First Silylation

The dry silica gel from Step 1 is transferred to a round-bottom flask and suspended in toluene (3.5 L). The flask is heated on a steam bath for 2 hours to azeotrope off some residual water. Octadecyltrichlorosilane (321 ml, Aldrich Chemical Company) is added, and the reaction mixture is refluxed overnight (16 hours) with slow mechanical stirring at about 60° C. Care is taken so that the stirrer does not reach near the bottom of the flask. This is to prevent grinding the silica gel particles.

The mixture is allowed to cool. The silanized silica gel is collected, washed with toluene (3 L) and acetone (3 L), and then air-dried overnight (16–20 hours). The dried silica gel is suspended in 3.5 L of acetonitrile:water (1:1) in a 5-L flask, stirred carefully at room temperature for 2 hours, filtered, washed with acetone (3 L) and air-dried overnight.

Step 3: Second Silylation

The procedure from the first silylation is repeated using 200 ml of octadecyltrichlorosilane. The suspension is refluxed at 60° C. for 2 hours while stirring carefully. The final product is recovered by filtration, washed with toluene (3 L) and methanol (6 L), and then dried under vacuum at 50° C. overnight (16–20 hours).

EXAMPLE 7

Slurry Packing Procedure for Michel-Miller Columns

General Information

This procedure is employed for packing silica gel $C_{18}$ reversed phase resin such as that prepared by the method of Example 6. Generally, a pressure of less than 200 psi and flow rates between 5–40 ml/minute are required for this slurry packing technique; this is dependent on column volume and size. Packing pressure should exceed the pressure used during actual separation by 30–50 psi; this will assure no further compression of the adsorbent during separation runs.

A sudden decrease in pressure may cause cracks or channels to form in the packing material, which would greatly reduce column efficiency. Therefore, it is important to let the pressure drop slowly to zero whenever the pump is turned off.

The approximate volume of columns (Ace Glass Cat. No., unpacked) are No. 5795-04, 12 ml; No. 5795-10, 110 ml; No. 5795-16, 300 ml; No. 5795-24, 635 ml; and No. 5796-34, 34 ml.

The time required to pack a glass column will vary from minutes to several hours depending on column size and the experience of the scientist.

Example:

1. Connect glass column to a reservoir column via coupling (volume of reservoir column should be twice that of the column). Place both columns in vertical positions (reservoir column above).

2. Weigh out packing material (ca. 100 g for 200 ml column).

3. Add ca. five volumes of solvent to packing material; use a mixture of 70–80% methanol and 20–30% water.

4. Shake well until all particles are wetted, let stand overnight or longer to assure complete soaking of particles by solvent. Decant supernatant liquid.

5. Slurry the resin with sufficient solvent to fill reservoir column. Pour swiftly into reservoir. The column must be pre-filled with the same solvent and the reservoir column should be partly filled with solvent before slurry is poured. The use of larger slurry volumes may also provide good results; however, this will require (a) larger reservoir or (b) multiple reservoir fillings during the packing procedure.

6. Close reservoir with the Teflon plug beneath the column (see FIG. 1 of U.S. Pat. No. 4,131,547, plug No. 3); connect to pump; and immediately start pumping solvent through system at maximum flow rate if Ace Cat. No. 13265-25 Pump or similar solvent-delivery system is used (ca. 20 ml/minute).

7. Continue until column is completely filled with adsorbent. Pressure should not exceed maximum tolerance of column during this operation (ca. 200 psi for large columns and 300 psi for analytical columns). In most cases, pressures less than 200 psi will be sufficient.

8. Should pressure exceed maximum values, reduce flow-rate; pressure will drop.

9. After column has been filled with adsorbent, turn off pump; let pressure drop to zero; disconnect reservoir; replace reservoir with a pre-column; fill pre-column with solvent and small amount of adsorbent; and pump at maximum pressure until column is completely packed. For additional information, see general procedure. Always allow pressure to decrease slowly after turning off pump—this will prevent formation of any cracks or channels in the packing material.

10. Relieve pressure and disconnect pre-column carefully. With small spatula remove a few mm (2–4) of packing from top of column; place 1 or 2 filter(s) in top of column; gently depress to top of packing material, and place Teflon plug on top of column until seal is confirmed. Connect column to pump, put pressure on (usually less than 200 psi) and observe through glass wall on top of column if resin is packing any further. If packing material should continue to settle (this may be the case with larger columns), some dead space or channelling will appear and step 9 should be repeated.

What is claimed is:

1. A compound of the formula:

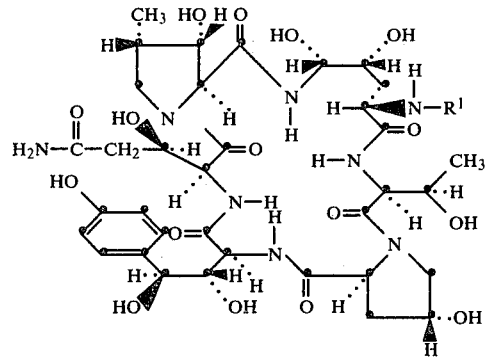

wherein $R^1$ is an N-alkanoyl amino acyl group of the formula

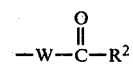

wherein:

W is a divalent aminoacyl radical of the formula:

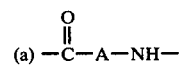

wherein A is $C_1$-$C_{10}$ alkylene or $C_5$-$C_6$ cycloalkylene:

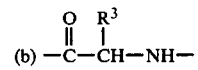

wherein $R^3$ is hydroxymethyl, hydroxyethyl, mercaptomethyl, mercaptoethyl, methylthioethyl, 2-thienyl, 3-indolemethyl, phenyl, benzyl, or substituted phenyl or substituted benzyl in which the benzene ring thereof is substituted with chloro, bromo, iodo, nitro, $C_1$-$C_3$ alkyl, hydroxy, $C_1$-$C_3$ alkylthio, carbamyl, or $C_1$-$C_3$ alkylcarbamyl;

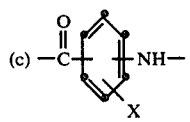

wherein X is hydrogen, chloro, bromo, iodo, nitro, $C_1$-$C_3$ alkyl, hydroxy, $C_1$-$C_3$ alkoxy, mercapto, $C_1$-$C_3$ alkylthio, carbamyl, or $C_1$-$C_3$ alkylcarbamyl;

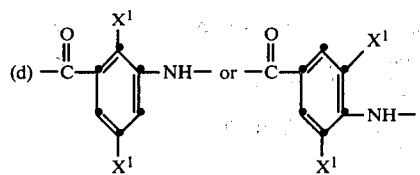

wherein $X^1$ is chloro, bromo, or iodo;

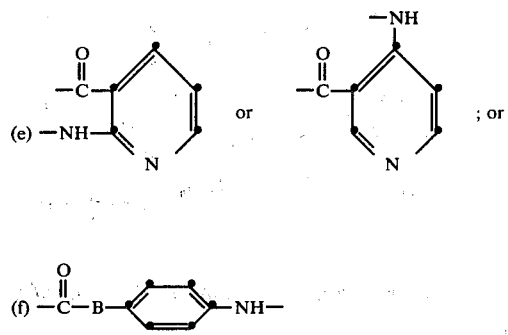

wherein B is a divalent radical of the formula:

—(CH$_2$)$_n$—, wherein n is an integer from 1 to 3; —CH=CH—; —CH=CH—CH$_2$—; or

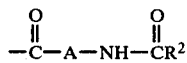

and $R^2$ is $C_1$–$C_{17}$ alkyl or $C_2$–$C_{17}$ alkenyl.

2. A compound as defined in claim 1 wherein $R^1$ is $$-\overset{O}{\underset{\|}{C}}-A-NH-\overset{O}{\underset{\|}{C}}R^2$$

wherein A is $C_1$–$C_{10}$ alkylene and $R^2$ is straight chain $C_1$–$C_{17}$ alkyl.

3. The compound as defined in claim 2 wherein $R^1$ is N-(n-dodecanoyl)-5-amino-n-pentanoyl.

4. The compound as defined in claim 2 wherein $R^1$ is N-(n-dodecanoyl)-11-amino-n-hendecanoyl.

5. The compound as defined in claim 2 wherein $R^1$ is N-(n-heptanoyl)-11-amino-n-hendecanoyl.

6. A compound as defined in claim 1 wherein $R^1$ is

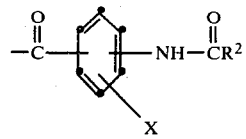

wherein X is hydrogen and $R^2$ is straight chain $C_1$–$C_{17}$ alkyl.

7. The compound as defined in claim 6 wherein $R^1$ is N-(n-dodecanoyl)-p-aminobenzoyl.

8. The compound as defined in claim 6 wherein $R^1$ is N-(n-dodecanoyl)-m-aminobenzoyl.

9. The compound as defined in claim 6 wherein $R^1$ is N-(acetyl)-p-aminobenzoyl.

10. The compound as defined in claim 6 wherein $R^1$ is N-(n-heptanoyl)-p-aminobenzoyl.

11. The compound as defined in claim 6 wherein $R^1$ is N-(n-decanoyl)-p-aminobenzoyl.

12. The compound as defined in claim 6 wherein $R^1$ is N-(n-tetradecanoyl)-p-aminobenzoyl.

13. The compound as defined in claim 6 wherein $R^1$ is N-(n-hexadecanoyl)-p-aminobenzoyl.

14. A compound as defined in claim 1 wherein $R^1$ is

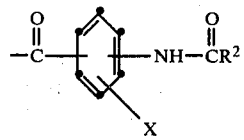

wherein X is chloro, bromo, iodo, nitro, $C_1$–$C_3$ alkyl, hydroxy, $C_1$–$C_3$ alkoxy, mercapto, $C_1$–$C_3$ alkylthio, carbamyl, or $C_1$–$C_3$ alkylcarbamyl and $R^2$ is straight chain $C_1$–$C_{17}$ alkyl.

15. The compound as defined in claim 14 wherein $R^1$ is N-(n-dodecanoyl)-4-amino-2-hydroxybenzoyl.

16. The compound as defined in claim 14 wherein $R^1$ is N-(n-dodecanoyl)-3-amino-4-methylbenzoyl.

17. The compound as defined in claim 14 wherein $R^1$ is N-(n-dodecanoyl)-4-amino-3-methylbenzoyl.

18. The compound as defined in claim 14 wherein $R^1$ is N-(n-dodecanoyl)-3-amino-4-methoxybenzoyl.

19. The compound as defined in claim 1 wherein $R^1$ is N-(n-dodecanoyl)-3-amino-2,5-dichlorobenzoyl.

20. The compound as defined in claim 1 wherein $R^1$ is N-(n-dodecanoyl)-4-amino-3,5-diiodobenzoyl.

21. The compound as defined in claim 1 wherein $R^1$ is N-(n-dodecanoyl)-p-aminophenylacetyl.

22. The compound as defined in claim 1 wherein $R^1$ is N-(n-dodecanoyl)-p-aminocinnamoyl.

23. The compound as defined in claim 1 wherein $R^1$ is N-(n-dodecanoyl)-p-aminohippuryl.

24. The compound as defined in claim 1 wherein $R^1$ is N-(n-dodecanoyl)-2-aminonicotinyl.

25. The compound as defined in claim 1 wherein $R^1$ is N-(n-dodecanoyl)phenylalanyl.

* * * * *